United States Patent
Friese et al.

(10) Patent No.: US 6,310,269 B1
(45) Date of Patent: Oct. 30, 2001

(54) TAMPON ESPECIALLY FOR FEMININE HYGIENE AND A PROCESS AND APPARATUS FOR PRODUCING THIS

(75) Inventors: Axel Friese, Durholzen (DE); Stefan Simon, Wiener Neudorf (AT)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 08/427,468

(22) Filed: Apr. 24, 1995

Related U.S. Application Data

(63) Continuation of application No. 08/124,374, filed on Sep. 20, 1993, now abandoned, which is a continuation of application No. 07/929,844, filed on Aug. 13, 1992, now abandoned, which is a continuation of application No. 07/799,922, filed on Nov. 26, 1991, now abandoned, which is a continuation of application No. 07/596,454, filed on Oct. 12, 1990, now abandoned.

(30) Foreign Application Priority Data

Oct. 12, 1989 (DE) ................................. 39 34 153

(51) Int. Cl.⁷ ............................ A61F 13/15; A61F 13/20; D04H 1/22
(52) U.S. Cl. .................... 604/379; 604/383; 604/385.17; 604/904; 28/118; 28/119
(58) Field of Search ...................... 604/285–286, 604/363, 378–380, 904; 28/116, 118–119, 125, 128–130, 136, 138–139, 120; 383/385.17, 315.18

(56) References Cited

U.S. PATENT DOCUMENTS

| | | |
|---|---|---|
| 2,152,230 | 3/1939 | Webb . |
| 2,188,423 | 2/1940 | Robinson . |
| 2,263,909 | 11/1941 | Webb . |
| 2,330,257 * | 9/1943 | Bailey ................................. 28/120 |
| 2,425,004 * | 8/1947 | Rabell .................................. 28/118 |
| 2,566,190 * | 8/1951 | Greiner et al. ....................... 28/118 |
| 2,798,260 | 7/1957 | Niepmann et al. . |
| 3,359,981 * | 12/1967 | Hochstrasser ....................... 604/379 |
| 3,422,496 * | 1/1969 | Wolff et al. .......................... 28/118 |
| 3,854,481 * | 12/1974 | Messing .............................. 604/904 |
| 4,109,354 * | 8/1978 | Ronc ................................... 28/119 |
| 4,175,561 * | 11/1979 | Hirschman ......................... 604/904 |
| 4,453,296 * | 6/1984 | Friese .................................. 28/119 |
| 4,498,218 * | 2/1985 | Friese .................................. 28/119 |
| 4,627,849 * | 12/1986 | Walton .............................. 604/388 |
| 4,675,217 | 6/1987 | Forsman . |
| 4,685,178 * | 8/1987 | Nakanishi ........................... 28/118 |
| 4,816,100 * | 3/1989 | Friese ................................ 604/904 |
| 5,165,152 * | 11/1992 | Kramer et al. ...................... 28/118 |
| 5,592,725 * | 1/1997 | Brinker .............................. 28/118 |

FOREIGN PATENT DOCUMENTS

| | | |
|---|---|---|
| 261771 | 8/1947 | (CH) . |
| 1491161 | 6/1969 | (DE) . |
| 26 23 368 | 11/1980 | (DE) . |
| 3606150 * | 8/1987 | (DE) ..................................... 28/118 |
| 1082770 | 9/1967 | (GB) . |
| 1548714 | 7/1979 | (GB) . |
| 2076656 * | 12/1981 | (GB) ................................... 604/904 |
| 83/03537 | 10/1983 | (WO) . |

OTHER PUBLICATIONS

EPO Search Report for Application No. 90119538.8.

* cited by examiner

Primary Examiner—John G. Weiss
Assistant Examiner—Karin Reichle

(57) ABSTRACT

A tampon having a relatively high density, compressed core (16) and a plurality of lower density longitudinal ribs (17) is disclosed. The longitudinal ribs (17) have a softer fiber structure and a coarser capillary structure and extend radially from the core (16). The longitudinal ribs (17) are separated one from another by outwardly open longitudinal grooves (18). A process for preparing the tampon and an apparatus useful in the process are also disclosed.

14 Claims, 6 Drawing Sheets

TAMPON ESPECIALLY FOR FEMININE HYGIENE AND A PROCESS AND APPARATUS FOR PRODUCING THIS

This is a continuation of application Ser. No. 08/124,374 filed Sep. 20, 1993 now abandoned, which is a continuation of application Ser. No. 07/929,844 now abandoned filed Aug. 13, 1992, which is continuation application Ser. No. 07/799,922 now abandoned, filed Nov. 26, 1991, which is a continuation application of Ser. No. 07/596,454, filed Oct. 12, 1990 now abandoned, which are hereby incorporated by reference and all abandoned.

BACKGROUND OF THE INVENTION

The invention relates to a tampon, especially for feminine hygiene, having a relatively high density compressed core and a plurality of lower density longitudinal ribs, as well as, to a process and an apparatus for producing the tampon.

A tampon of the abovementioned generic type is known from German Auslegeschrift 1,491,161. This tampon has proved appropriate in practice because of its high absorption capacity, fluid retention capacity, rate of absorption, stability and buckling strength. For this, the tampon has longitudinal grooves which are caused by pointed press jaws and on each of the two sides of which occur longitudinal ribs which are pressed to the approximately cylindrical final form of the tampon during a subsequent pressing operation by means of press jaws with partially cylindrical press faces.

SUMMARY OF THE INVENTION

The object on which the invention is based is to improve the tampon of the abovementioned generic type in such a way that the absorption capacity and rate of absorption of the tampon appertaining to the two are essentially maintained, but the specific absorption capacity of the tampon is increased.

This and other objects are achieved by the tampon having disclosed that makes it possible to obtain an appreciable increase in the specific absorption capacity (ml/g), whilst preserving the hitherto obtained absorption capacity and rate of absorption, with a surprisingly smaller amount of fibre material being used. This effect is attributable to a coarser capillary structure of the fibre material in the outer layer of the tampon.

Thus, it was found that a tampon according to the invention consisting of 100% rayon fibres with a weight of 2.4 g without the withdrawal string can have a specific absorption capacity of 4.8 ml/g with a rate of absorption of 1.9 ml/s. The absorption capacity of such a tampon at a static counterpressure of 20 mbars is 11.3 ml. In a test with a pulsating counterpressure of 20 to 110 mbars approximating extremely closely to the practical conditions of use, the absorption capacity of the tampon according to the invention can amount to 8.0 ml and the specific absorption capacity to 3.4 ml/g.

The diameter of the tampon is set at between 13 and 15 mm according to the customary physiological conditions, and the central fibre core can preferably have a diameter of 4 to 8 mm. A high buckling strength of the tampon can thus be achieved, whilst at the same time the soft surface of the tampon guarantees a pleasant handling of the tampon.

The invention relates, furthermore, to a process for producing this tampon A process of this type is known from German Auslegeschrift 1,491,161 already mentioned.

According to the invention, this process for producing the tampon according to the invention is improved by means of pressing only narrow strip-shaped portions of the surface of the blank.

The invention relates, moreover, to an apparatus for producing the tampon and for carrying out the abovementioned process. An apparatus of this generic type is likewise known from German Auslegeschrift 1,491,161. According to the invention, this known apparatus is improved, with the effect of the best possible production of the tampon according to the invention. The fact that only press cutters are provided on the end faces of the segment-shaped pressed jaws and of the sliding plates guarantees a merely partial pressing of the winding blank to produce a preform which is subsequently subjected only to a weak concentric shaping in the following forming die, thereby providing a smooth, soft and aesthetically pleasing surface of the tampon, but which, despite the use of a smaller amount of fibre material, allows an appreciably increased specific absorption capacity of the tampon, without the tampon suffering from a loss of absolute absorption capacity in comparison with the known tampon mentioned.

The apparatus according to the invention is advantageously developed by means of the features mentioned in the subclaims.

BRIEF DESCRIPTION OF THE DRAWINGS

The invention is explained in more detail below by means of the diagrammatic drawing of an exemplary embodiment of a tampon and of an apparatus for producing this. In the drawing:

FIGS. 6 and 7 show a separate closing movement of the pressing dies, wherein FIG. 6 illustrates a first pressing face of the preforming press with closed press segments, whilst a second, final press face of the preforming press is illustrated in FIG. 7 showing the sliding plates in the closed position, wherein all press dies enclose the preform arranged in it, FIG. 8 shows an interphase of the pressing procedure and FIG. 9 the press dies completely closed with the preform arranged in it.

DESCRIPTION OF THE PREFERRED EMBODIMENT

Figure 1:
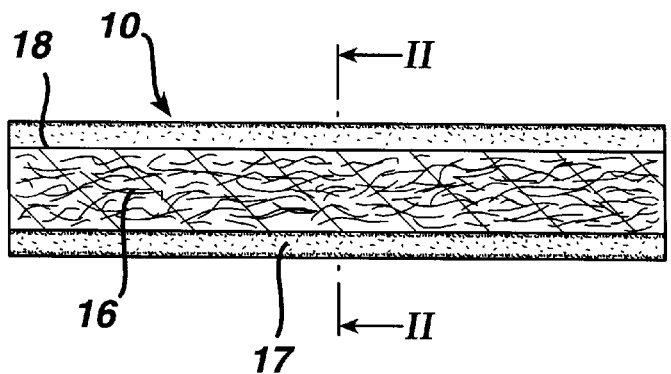
FIG. 1 shows the tampon according to the invention in a middle longitudinal section along the sectional line I—I in FIG. 2.
Figure 2:
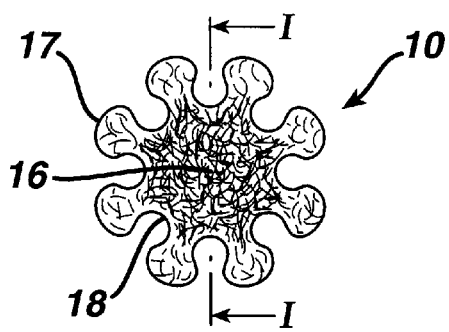
FIG. 2 shows a cross-section along sectional line II—II shown in FIG. 1, showing heavy outwardly open grooves the tampon of the current invention.

FIGS. 1 and 2 show a tampon 10 for feminine hygiene formed from an approximately cylindrical blank 11 which is shaped by winding up a portion of length of nonwoven material, needled if appropriate. The nonwoven can consist of natural or synthetic fibres or of a mixture of such fibres. Natural fibres coming under consideration are preferably those of cotton. Rayon or other synthetic fibres are also highly suitable. The circumferential surface of this winding blank is pressed in a way known per se radially relative to the longitudinal mid-axis of the winding blank over an even number of at least six, preferably eight portions mutually adjacent in the circumferential direction of the winding blank 11.

Figure 3:
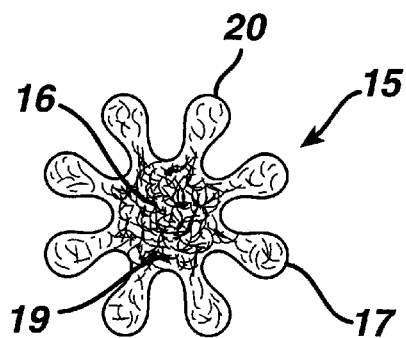
FIG. 3 shows a cross-section through the preform along the line III—III in FIG. 10.
Figure 7:
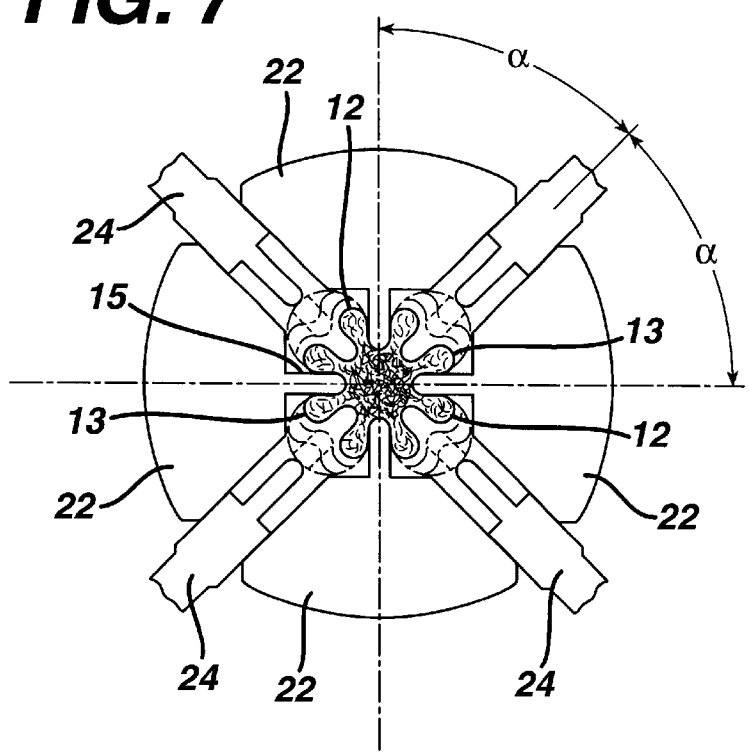
Figure 9:
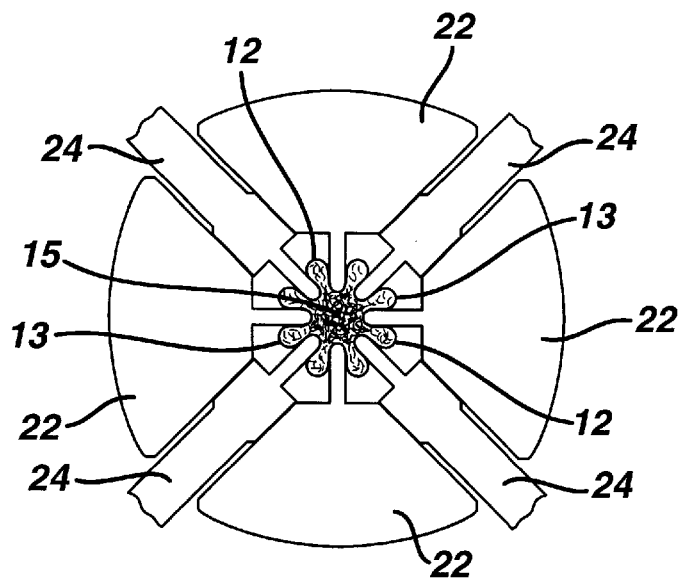

According to the invention, these circumferential portions of the winding blank 11 are exclusively narrow strip-shaped portions 12, 13 of the circumferential surface 14 of the winding blank 11 which are arranged at equal angular distances a from one another and which are pressed to produce a preform 15 in FIGS. 3, 7 and 9. As seen in cross-section, the preform 15 consists of a central approximately circular fibre core 16 of high compression and stability or buckling strength and of longitudinal ribs 17 extending radially outwards from the fibre core 16 and of a fibre structure softer than that of the fibre core and of correspondingly coarser capillary structure (FIG. 3). The longitudinal ribs 17 are separated from one another by outwardly open longitudinal grooves 18. Only the soft longitudinal ribs 17 of the preform 15 are exposed to a low uniform radial pressure during manufacture relative to the longitudinal mid-axis 19 of the preform 15, in such a way that the radially outer ends 20 of the longitudinal ribs 17 form a soft essentially smoothly cylindrical surface of smaller diameter corresponding to the final form of the tampon 10.

It was found that the tampon according to the invention has a stability 100% higher than that of the known tampon. It was shown, furthermore, that approximately 10% of the fibres used for the tampon can be saved, without any appreciable impairment, if any, of the absorption capacity. In contrast, the rate of absorption is in the upper range of known tampons, whilst the specific absorption capacity is increased appreciably in relation to known tampons.

The following table illustrates a comparative test of the tampon according to the invention consisting of a needled nonwoven composed of 100% of rayon fibres from Hoechst AG, and a tampon obtainable in the trade under the commercial designation "Standard O.B.":

TABLE

| | Tampon according to the invention | STANDARD O.B. Tampon |
|---|---|---|
| 1. Weight (g) without the withdrawal string | 2.4 | 2.7 |
| 2. Absorption capacity (ml) 20 mbars static counterpressure in test unit | 11.3 | 11.5–12.5 |
| 3. Specific absorption capacity (ml/g) | 4.8 | 4.2–4.5 |
| 4. Rate of absorption (ml/s) | 1.9 | 1.5–2.0 |
| 5. Absorption capacity (ml) in ABTS test unit with pulsating counterpressure of 20–110 mbars | 8.0 | 8.6 |
| 6. Specific absorption capacity (ml/g) in ABTS test unit | 3.4 | 3.1 |

The absorption capacity values indicated in line 2 of the Table were determined in a test unit, in which the tampon is surrounded by an elastic diaphragm which exerts a static counterpressure on the tampon, whilst one end of the tampon is sprinkled with water. This resulted in the specific fluid absorption capacity in ml/g of fibre material of the tampon evident from line 3 of the Table.

The rate of absorption emerging from line 4 was determined in this test arrangement. The values show that, at a weight of the tampon according to the invention reduced by approximately 10%, the absorption capacity of the tampon is not essentially reduced in relation to the known tampon, the rate of absorption is of the upper limit of that of the known tampon, and the specific absorption capacity is appreciably higher than in the known tampon. Since the specific absorption capacity is evidence of a better utilization of the absorbency of the fibre material per unit weight, it is clear that the tampon according to the invention can be produced more cheaply as a result of the lower weight of material.

Lines 5 and 6 of the Table give values for the absorption capacity and the specific absorption capacity determined in a test arrangement allowing test conditions such as actually occur when the tampon is being worn.

The system designated as ABTS, corresponding to Absorptive Behaviour Test System, is computer-assisted and serves for the acquisition and processing of measurement data regarding the absorption behaviour of absorbent products and for controlling the test cycle.

The test of the tampon is conducted under the following conditions which, as mentioned, occur approximately in vivo:

chemical/physical compositions of the test fluid
  spacial arrangement of the product, for example inclination
  positioning of the product in the measuring cell
  strength of the flow
  interruption (start/stop) of the flow
  pressure variant.

The test cycle is software-controlled automatically and allows a dialogue between the operator and system. The measurement data are required automatically, their evaluation taking place according to statistical factors. The test cycle for each random sample can be tracked on a video screen by means of a measurement curve and, if appropriate, printed out automatically. Furthermore, the fluid distribution in the product is represented qualitatively and quantitatively. Moreover, the leakage behaviour of the tampon can be checked. By leakage is meant the phenomenon in which menstrual fluid can escape between the body wall and tampon. The feed of test fluid to the tampon is carried out exclusively without pressure, since the fluid level is at the height of the test tampon. The fluid is therefore sucked up into the tampon solely as a result of the wetting of the tampon and the wick effect caused by the capillary forces of the latter, and by means of the pulsating counterpressure on the tampon which is felt in practice.

The values determined with this ABTS test device illustrate, in lines 5 and 6 of the Table, that, at the pulsating counterpressure indicated, the absorption capacity of the tampon is only slightly lower than in the reference tampon, but here too the specific absorption capacity of the tampon according to the invention per gram of fibre material is approximately 10% higher than in the reference tampon.

The diameter of the tampon according to the invention is between 13 and 15 mm in its final form. The central fibre core 16 has a diameter of approximately 4 to 8 mm.

Figure 4:
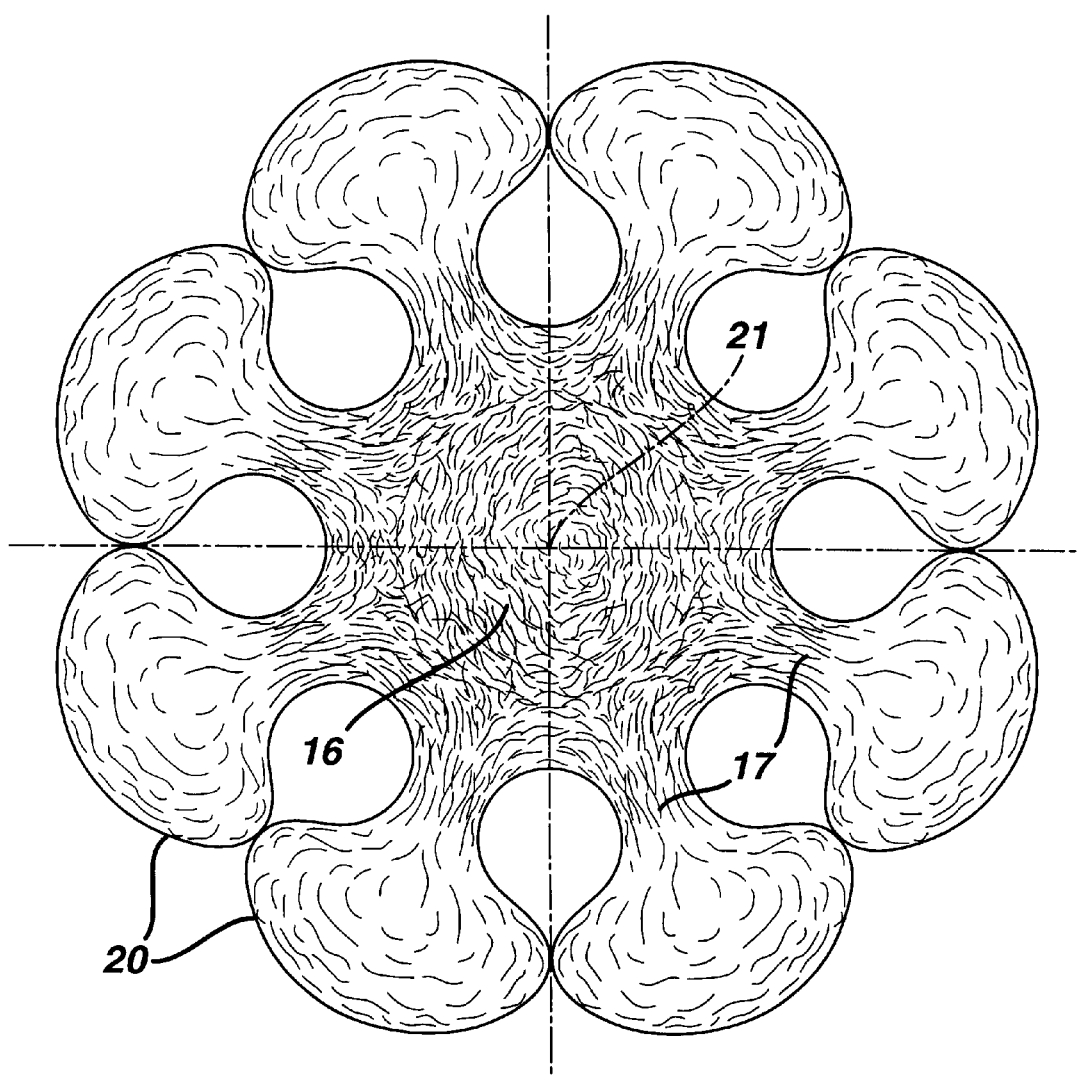
FIG. 4 shows a cross-section of the tampon of the invention, heavy closed grooves.

FIG. 4 shows an enlarged cross-sectional representation of the fibre structure of the tampon according to the invention. It is possible to see clearly the central fibre core 16, from which extend outwards eight longitudinal ribs 17 touching one another at their outer ends 20. The tampon cross-section shows, moreover, that the loose fibre structure with its coarser capillary structure of the longitudinal ribs 17 is preserved, despite the concentric pressure to which these longitudinal ribs are exposed during the production of the final form of the tampon. In contrast, the fibre core 16 having a high fibre compression guarantees a stability or buckling strength which is twice as high as that of the reference tampon and which is of great importance when the tampon is used as a digital tampon.

Figure 5:
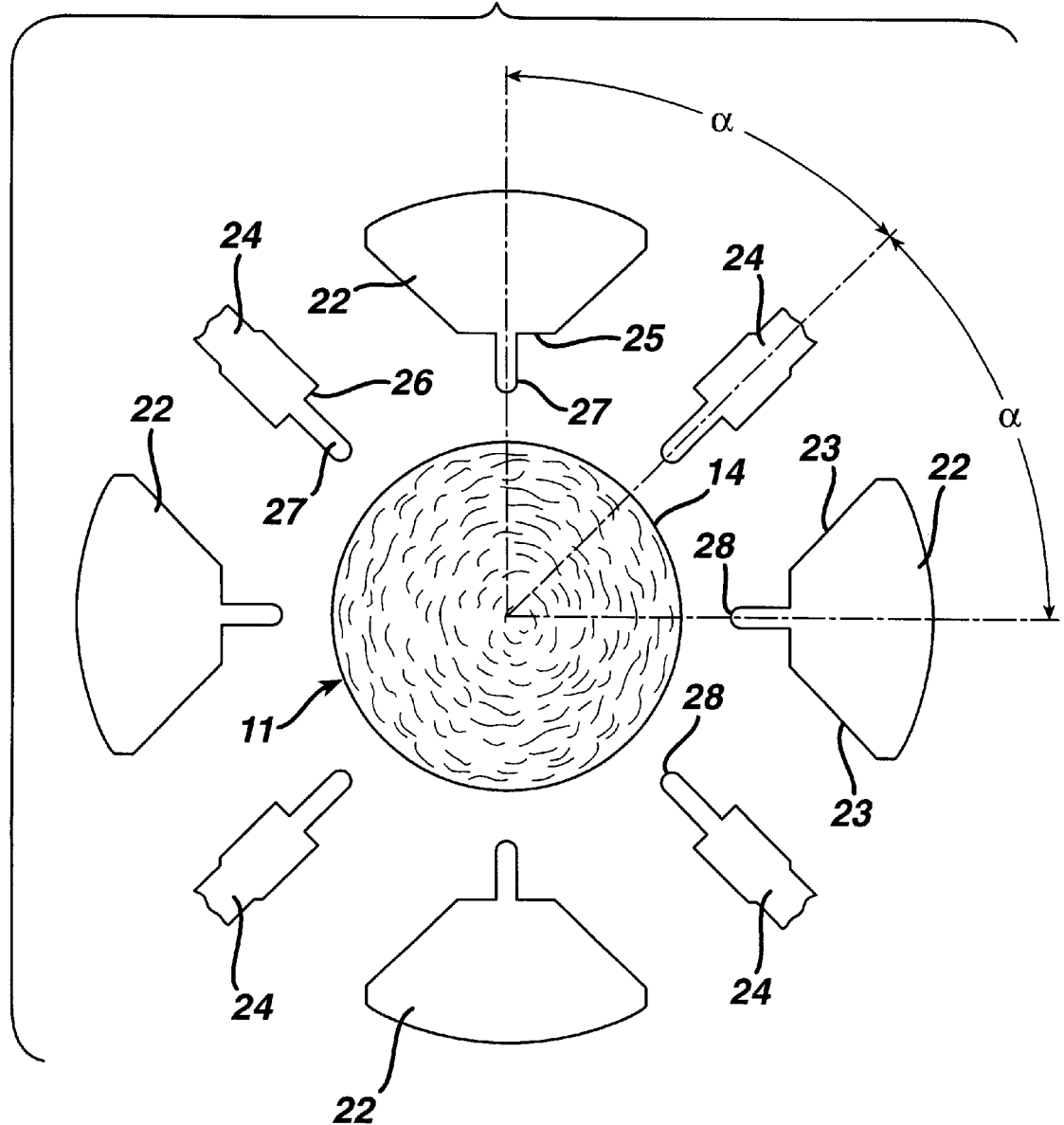
FIG. 5 shows a diagrammatic view of a preforming press in the opened state with a winding blank arranged in it.

The figures illustrate an apparatus according to the invention for producing the tampon. According to FIGS. 5 to 7, this apparatus consists of two groups of altogether eight press dies arranged in a plane perpendicular to the press axis 21, the first group of press dies forming press segments 22 and the second group of press dies forming sliding plates 24. In the closing position shown in FIG. 6, the side flanks 23 of these four press segments 22 form respectively for each of the four press dies of the second group guide surfaces which are designed as sliding plates 24. At the same time, the press segments 22 and the sliding plates 24 serve, as a preforming press, for pressing the winding blank 11 to produce the preform 15 in FIG. 7. Exclusively press cutters 27 projecting from the end faces 25 and 26 of the press segments 22 and of the sliding plates 24 serve for pressing the blank. It is evident from FIGS. 5 to 7 that the press cutters project from the end faces 25 and 26 of the press segments 22 and sliding plates 24 at equal angular distances and over the same length. The shape and dimensions of all the press cutters are identical. The press cutters are therefore also equipped at their front end with the same pressing faces 28 which, in the exemplary embodiment illustrated, each extend parallel to the press axis and are curved outwards in the manner of a semi-cylinder.

In the exemplary embodiment, the length and width of the press cutters 27 radial relative to the press axis 21 amount to 10 mm and 2 mm respectively. In the closed state of the preforming press, the pressing faces 28 of the press cutters 27 assume a clear distance of 2 to 4 mm from the press axis 21 (FIG. 10).

Figure 6:
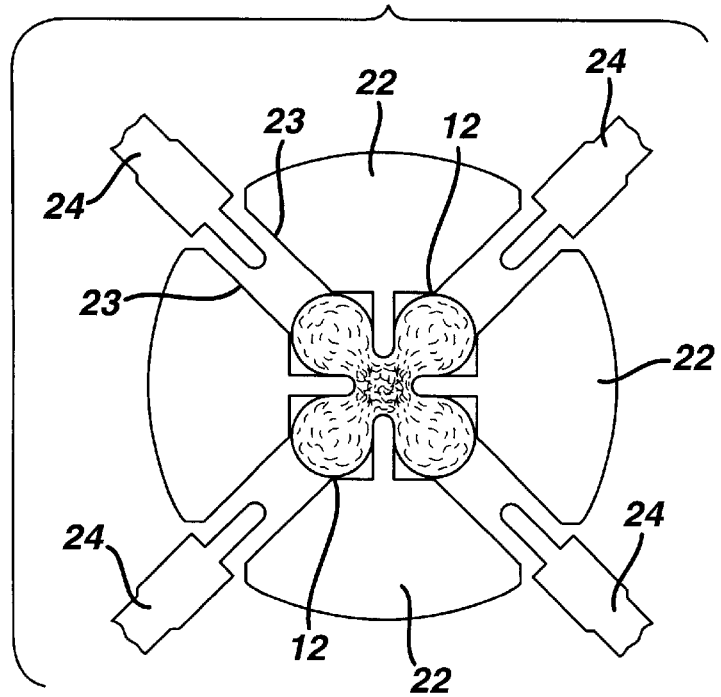
Figure 8:
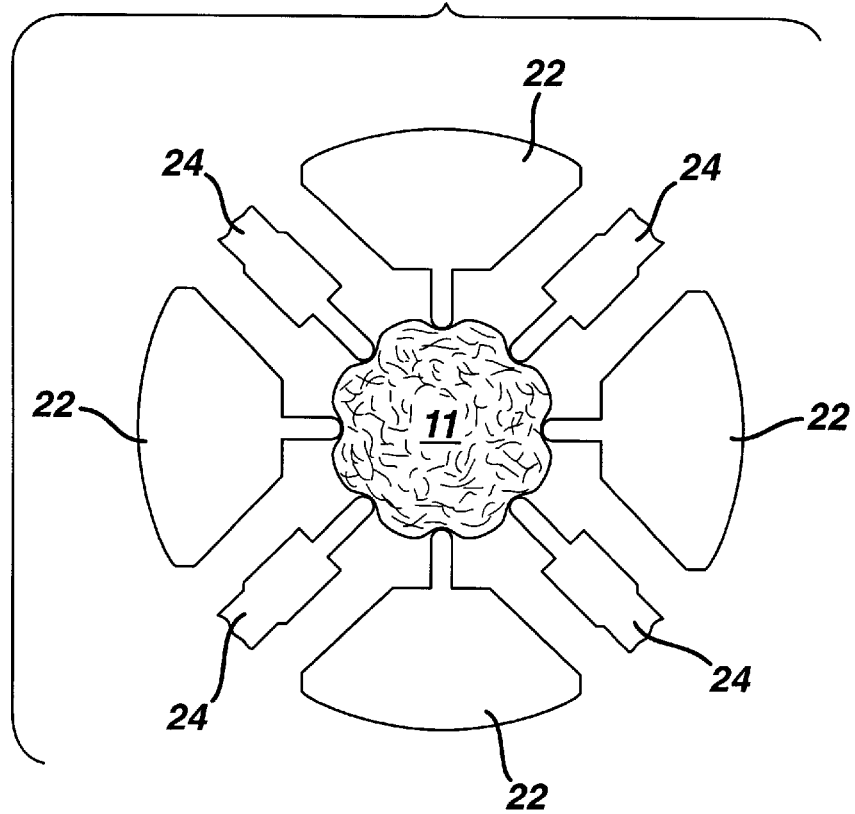
FIGS. 8 and 9 show an alternative sequence of movements of the press dies, wherein the press segments and the sliding plates are simultaneously moved into the closed position.

In contrast with FIGS. 6 and 7, FIGS. 8 and 9 show a synchronous closing movement of the press segments 22 and sliding plates 24 in the radial direction. FIG. 8 shows an intermediate phase of this closing movement of the press dies, whilst the final closing position of these press dies is shown in FIG. 9. The position of the dies shown in FIG. 9 corresponds to the final dimension of the preform 15. The simultaneous pressing movement of the press segments 22 and the sliding plates 24 has the advantage, that the geometrical uniformity of the circumferential strip-shaped portions 12 and 13 of the preform 15 will be enhanced. If the tampon is wetted by a fluid the tampon will expand to a more circular shape than in case of the sequential movement of the press dies as shown in FIGS. 6 and 7.

If appropriate, however, the press faces can also have a mutually differing shape. If appropriate, the sliding plates can also be designed differently, for example made angular, arrow-shaped or drop-shaped. It is essential that they load and press only a narrow circumferential portion of the blank corresponding approximately to a generatrix. Furthermore, the cycle of movement of the two groups of press dies can, where appropriate, also take place simultaneously or interruptedly in the preforming and post forming and alternately between these two movement actions. Thus, it can be important, according to the process of German Auslegeschrift 1,491,161, first to close all the press dies simultaneously only up to the circumference of the blank 11, in order to centre the blank as exact as possible in relation to the press axis 21, before commencing the actual pressing operation, so as to ensure that the central fibre core 16 comes to rest exactly in the middle of the tampon 10. This is desirable to obtain the highest possible buckling strength or stability of the tampon, above all when the latter is to be used as a digital tampon.

Figure 10:
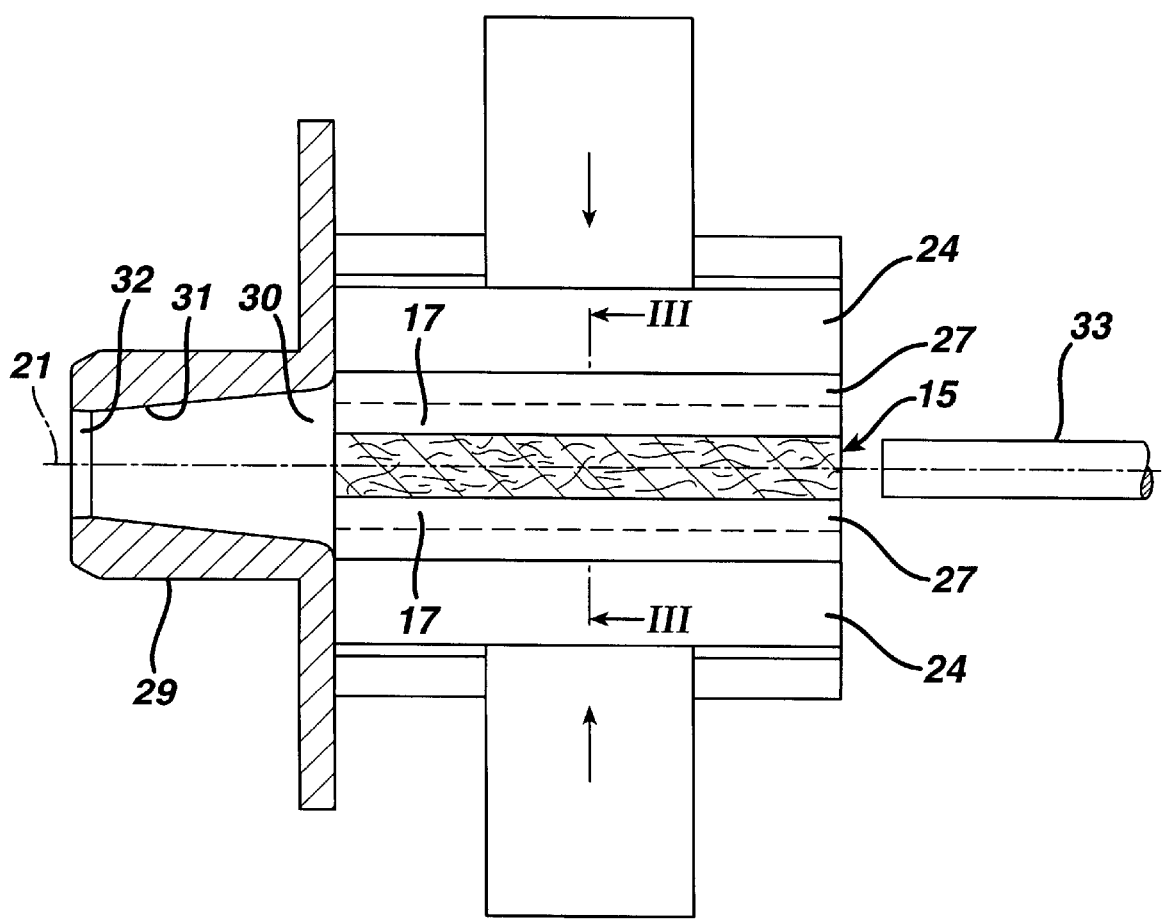
FIG. 10 shows a partially sectional side view of the apparatus for producing the tampon with the preforming press and with the following forming die.

According to FIG. 10, the preforming press described is followed by a stationary conical forming die 29. This forming die 29 is arranged coaxially relative to the press axis 21. The entry orifice 30 of the forming die has a diameter of 20 mm which corresponds approximately to the orifice of the preforming press in the closed state of its press dies which is shown in FIG. 7. The inner face 31 is narrowed towards the cylindrical exit orifice 32 according to an obtuse-angled circular cone, the exit orifice 32 has a diameter of 13 mm and its cross-section corresponds to the final cross-section of the finished tampon 10. Arranged on the input side of the preforming press is a ram 33 which serves for introducing the winding blank 11 into the preforming press and for ejecting the preform 15 through the forming die 29. For this purpose, the ram 33 is arranged movably to and fro coaxially in relation to the press axis 21. Rams of this type are known in the art, and therefore there is no need to represent the driving elements for the ram.

The production of the tampon according to the invention by means of the above-described apparatus is carried out according to the following process: the essentially cylindrical winding blank 11 is pressed solely on the narrow strip-shaped portions 12 and 13, arranged at equal angular distances from one another, of the circumferential surface of the winding blank, to produce the preform 15 which, as seen in cross-section, consists of the central approximately circular fibre core 16 of high compression and buckling strength or stability and of longitudinal ribs 17 of softer fibre structure extending radially outwards from the fibre core 16. At the same time, the longitudinal ribs 17 are separated from one another by the outwardly open longitudinal grooves 18. Thereafter, only the soft longitudinal ribs 17 of the preform 15 are exposed to a low uniform pressure radial relative to the longitudinal mid-axis of the preform, until the outer ends of the longitudinal ribs have produced a soft essentially smoothly cylindrical surface of smaller diameter corresponding to the final form of the tampon 10. As mentioned, preferably before the actual pressing, the winding blank 11 is centred relative to the press axis 21 of the preforming press as a result of the simultaneous concentric closing of the press segments 22 and sliding plate 24 approximately as far as the circumference of the winding blank.

After the pressing of the preform, the latter is ejected through the forming die 29 by means of the ram 33 and thereby brought to the final dimension of the tampon which is determined by the exit orifice 32 of the forming die 29.

What is claimed is:

1. A tampon for feminine hygiene, comprising a generally cylindrical absorbent portion having a generally cylindrical compressed, solid fibre core from which longitudinal ribs extend radially outward, wherein each of the ribs has a proximal end attached to the fibre core, each of the ribs is compressed less than the fiber core, thereby having a coarser capillary structure than the fibre core, each of the ribs is separated from adjacent ribs at the proximal end by an amount greater than such rib is separated from an adjacent longitudinal rib proximate the distal end.

2. The tampon of claim 1, wherein the absorbent portion comprises a needled nonwoven material.

3. The tampon of claim 1, wherein each of the longitudinal ribs contacts an adjacent longitudinal rib at a point adjacent its distal end.

4. The tampon of claim 1, wherein the compressed fiber core has a diameter of 4 to 8 mm.

5. An apparatus for producing a tampon from an approximately cylindrical tampon blank, comprising: (i) first and second groups of press dies, at least three press dies in each group, the press dies arranged in a plane perpendicular to a longitudinal press axis and adapted to move radially inward toward the longitudinal press axis into a closed position so as to press the tampon blank into a tampon preform, the first group of press dies having side flanks so that when the first group of press dies are in the closed position their side flanks form guide surfaces for each of the second group of press dies, each of the press dies having an end face, the end faces collectively forming a generally cylindrical surface having a diameter when the press dies are in the closed position, each of the press dies having a press cutter having a distal end projecting from its end face toward the longitudinal press axis, the distal ends of the press cutters are extended to an essentially equal radial distance from the longitudinal press axis in forming the tampon preform, each of the press cutters adapted to form a groove in the tampon preform, leaving ribs extending outward from the longitudinal press axis between adjacent grooves, the ribs each having a distal end; and (ii) a stationary conical forming die arranged coaxially relative to the longitudinal press axis for softening the distal ends of the ribs, the forming die having an entry orifice having a diameter that approximately corresponds to the diameter of the generally cylindrical surface formed by the end faces of the press dies in the closed position, and a smaller exit orifice.

6. Apparatus according to claim 5, wherein each press cutter projects radially inward from the press die ends face by an equal distance and is separated from its respective adjacent press cutter by an equal angular amount ($\alpha$).

7. Apparatus according to claim 6, wherein the end face of each of the press dies has the same shape.

8. Apparatus according to claim 7, wherein each press cutter has a longitudinally extending curved face.

9. Apparatus according to claim 5, wherein the length of each of the press cutters in the longitudinal direction and the width of each of the press cutters in the radial direction are about 10 mm and 2 mm, respectively.

10. Apparatus according to claim 9, wherein when the press dies are in the closed position, the distal ends of the press cutters are disposed 2 to 4 mm from the longitudinal axis.

11. Apparatus according to claim 5, wherein the entry orifice has a diameter of 20 mm and the exit orifice has a diameter of 13 mm.

12. Apparatus according to claim 11, wherein the approximately cylindrical tampon blank has a diameter and all the press dies are adapted to move radially inward to approximately the diameter of the tampon blank, the press dies of the first group being adapted to move further radially inward into the closed position before the press dies of the second group move further radially inward.

13. Apparatus according to claim 11, wherein all of the press dies are adapted to simultaneously move radially inward into the closed position.

14. Apparatus according to claims 13, further comprising (i) an input end adapted to receive the blank, and (ii) a ram arranged on the input end, the ram being axially movable for pushing the preform through the conical forming die.

* * * * *

(12) EX PARTE REEXAMINATION CERTIFICATE (7591st)
United States Patent
Friese et al.

(10) Number: US 6,310,269 C1
(45) Certificate Issued: Jul. 6, 2010

(54) TAMPON ESPECIALLY FOR FEMININE HYGIENE AND A PROCESS AND APPARATUS FOR PRODUCING THIS

(75) Inventors: Axel Friese, Durholzen (DE); Stefan Simon, Wiener Neudorf (AT)

(73) Assignee: McNeil-PPC, Inc., Skillman, NJ (US)

Reexamination Request:
No. 90/006,467, Nov. 27, 2002

Reexamination Certificate for:
Patent No.: 6,310,269
Issued: Oct. 30, 2001
Appl. No.: 08/427,468
Filed: Apr. 24, 1995

Related U.S. Application Data

(63) Continuation of application No. 08/124,374, filed on Sep. 20, 1993, now abandoned, which is a continuation of application No. 07/929,844, filed on Aug. 13, 1992, now abandoned, which is a continuation of application No. 07/799,922, filed on Nov. 26, 1991, now abandoned, which is a continuation of application No. 07/596,454, filed on Oct. 12, 1990, now abandoned.

(30) Foreign Application Priority Data

Oct. 12, 1989 (DE) .......................................... 39 34 153

(51) Int. Cl.
*A61F 13/20* (2006.01)
*A61F 13/15* (2006.01)

(52) U.S. Cl. .................. 604/379; 604/383; 604/385.17; 604/904; 28/118; 28/119

(58) Field of Classification Search ........................ None
See application file for complete search history.

(56) References Cited

U.S. PATENT DOCUMENTS

| | | | |
|---|---|---|---|
| 2,152,230 A | 3/1939 | Webb | 18/55 |
| 2,188,423 A | 1/1940 | Andrews | 29/155.54 |
| 2,263,909 A | 11/1941 | Webb | 18/16 |
| 2,566,190 A | 8/1951 | Greiner et al. | 19/144 |
| 2,798,260 A | 7/1957 | Niepmann et al. | 19/144.5 |
| 3,359,981 A | 12/1967 | Hochstrasser | 128/285 |
| 3,854,481 A | 12/1974 | Messing | 128/285 |
| 4,109,354 A | 8/1978 | Ronc | 28/119 |
| 4,222,381 A | 9/1980 | Widlund et al. | 128/270 |
| 4,627,849 A | 12/1986 | Walton et al. | 604/379 |
| 4,685,178 A | 8/1987 | Nakanishi | 28/118 |
| 5,165,152 A | 11/1992 | Kramer et al. | 28/118 |

FOREIGN PATENT DOCUMENTS

| | | |
|---|---|---|
| DE | 30 15 730 A1 | 10/1981 |
| DE | 31 18 824 A1 | 4/1982 |
| DE | 36 06 150 A1 | 8/1987 |
| DE | 37 17 897 A1 | 12/1988 |
| GB | 1283708 | 8/1972 |
| GB | 2 076 656 A | 12/1981 |
| JP | 48/41637 | 12/1973 |
| JP | 57-190560 | 11/1982 |
| JP | 60-909 | 1/1985 |

OTHER PUBLICATIONS

Unexamined Utility Model 55–168330[1980], Application For Utility Model Registration, "A Sanitary Tampon", English Language Abstract Provided, Translated from Japanese.

*Primary Examiner*—David O. Reip

(57) ABSTRACT

A tampon having a relatively high density, compressed core (16) and a plurality of lower density longitudinal ribs (17) is disclosed. The longitudinal ribs (17) have a softer fiber structure and a coarser capillary structure and extend radially from the core (16). The longitudinal ribs (17) are separated one from another by outwardly open longitudinal grooves (18). A process for preparing the tampon and an apparatus useful in the process are also disclosed.

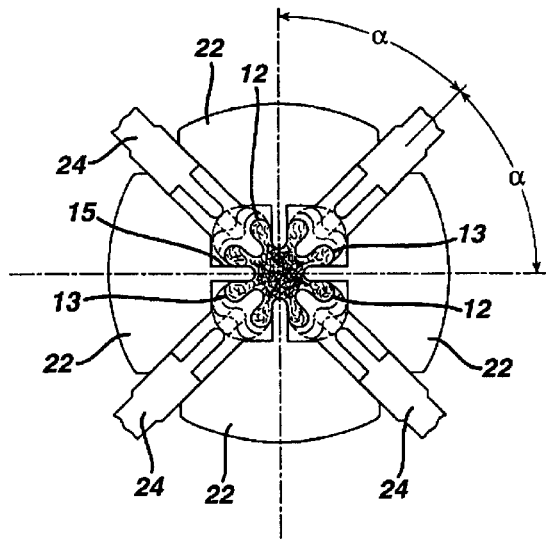

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-14 is confirmed.

* * * * *